(12) United States Patent
Lee

(10) Patent No.: US 6,414,166 B1
(45) Date of Patent: Jul. 2, 2002

(54) PROCESS FOR PREPARING TOCOPHEROL CONCENTRATES

(75) Inventor: Min-Hsiung Lee, Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/474,792

(22) Filed: Dec. 29, 1999

(51) Int. Cl.⁷ ............................................. C07D 311/72

(52) U.S. Cl. ...................................... 549/408; 549/513

(58) Field of Search ................................ 549/408, 413

(56) References Cited

U.S. PATENT DOCUMENTS

| | | | |
|---|---|---|---|
| 3,335,154 A | * | 8/1967 | Smith et al. |
| 4,454,329 A | | 6/1984 | Takagi et al. |
| 4,594,437 A | | 6/1986 | Sampathkumar |
| 5,190,618 A | | 3/1993 | Top et al. |
| 5,616,735 A | | 4/1997 | Hunt |
| 5,627,289 A | | 5/1997 | Jeromin et al. |
| 5,703,252 A | | 12/1997 | Hunt et al. |

OTHER PUBLICATIONS

Lee et al., "Concentration of oTocopherols From Soybean Sludge by Supercritical Carbon Dioxide," JAOCS, vol. 68 (No. 8), p. 3, (Dec. 29, 1991).

Mau et al., "Investigation on the Conditions for the preparation of High–Purity Vitamin E Concentrate from Soybean Oil Deodorizer Distillate," national Chung Hsing University (Taiwan, ROC), p. 12, (Dec. 29, 1995).

* cited by examiner

*Primary Examiner*—T. A. Solola
(74) *Attorney, Agent, or Firm*—Gene Scott-Patent Law & Venture Group

(57) ABSTRACT

This invention relates to a process for the preparation of tocopherol concentrates from a material containing tocopherols and free fatty acids. The free fatty acids in the tocopherol-containing material are converted to the alkali metal salts thereof in a specific organic solvent that can not, practically, dissolve the alkali metal salts of fatty acids. The free fatty acids are removed as a precipitate of their alkali salts, and the tocopherols are recovered from the supernatant by removing the solvent. The said specific organic solvents include acetone, ethyl acetate, dimethylformamide, acetonitrile and their mixtures. The alkali salts are preferably sodium and potassium salts.

11 Claims, 3 Drawing Sheets

PROCESS FOR PREPARING TOCOPHEROL CONCENTRATES

FIELD OF THE INVENTION

This invention relates to a simple and effective process for preparing tocopherol concentrates.

BACKGROUND OF THE INVENTION

Vegetable oil deodorizer sludge contains about 5 to 20% of tocopherols, and therefore is an important raw material for producing vitamin E and the natural antioxidants. However, the deodorizer sludge often contains substantial amount of free fatty acids, glycerides, phytosterols and hydrocarbons. The contents of free fatty acids are considerably high, ranging from about 30 to 60%. Thus, when we prepare the tocopherol concentrates from the vegetable oil deodorizer sludge, it is essential to remove these substances first, especially the free fatty acids.

Many methods for preparing tocopherol concentrates have been reported. Most of these methods involve esterification (especially methyl esterification) and high-temperature molecular distillation. The steps for such methods are very complex and require using the expensive distillation equipment and operating at a high temperature which might be a disadvantage to the heat-labile tocopherols. These methods can be mentioned as, for example, Mao and Tsen's method (Investigation on the Conditions for the Preparing of High-Purity Vitamin E Concentrate from Soybean Oil Deodorizer Distillate. *Journal of the Chinese Agricultural Chemical Society.* 33(6): 686–697, 1995, Taipei), and the methods disclosed in U.S. Pat. No. 4,454,329. (Y. Takagi and Y. Kai, Process for preparation of tocopherol concentrates. Jun. 12, 1984); U.S. Pat. No. 5,190,618 (A. G. Md. Top, et. al., Production of high concentration tocopherols and tocopherols from palm-oil by-products. Mar. 2, 1993); U.S. Pat. No. 5,616,735 (T. K. Hunt, Recovery of tocopherols. Apr. 1, 1997); U.S. Pat. No. 5,627,289 (L. J. Hilden, et. al., Recovery of tocopherol and sterol from tocopherol and sterol containing mixtures of fats and fat derivatives. May 6, 1997), and U.S. Pat. No. 5,703,252 (T. K. Hunt and J. Schwarzer, Recovery of tocopherols. Dec. 30, 1997), etc. All these methods are principally using esterification in combination with molecular distillation. These processes are all complicated, time-consuming and require high temperature treatment and expensive equipment.

On the other hand, U.S. Pat. No. 4,594,437 (Sampathkumar, Jun. 10, 1986) disclosed a process for recovering tocopherols from deodorizer sludge by using large amounts of solvent and urea to remove free fatty acids. According to the claim 1 of this patent, the amount of urea used is 5 to 25 equivalents of the fatty acids, and the amount of the solvent is 1 to 75 equivalents of urea. In additions, this method also includes heating at about 70° C. and cooling to 0° C., and this is very energy consuming. Furthermore, in order to recover the tocopherols, it needs to use other solvents to extract the tocopherols, for example, $CHCl_3$ in Example 1; hexane in Example 2; $CH_2Cl_2$ in Example 3.

In additions, Lee, et al. reported a method for the concentration of tocopherols from soybean oil sludge by supercritical carbon dioxide [*J Am. Oil Chem. Soc.* 68(8): pp. 571–573, 1991]. However, this method also requires esterification of free fatty acids and an expensive special equipment for the supercritical carbon dioxide extraction.

SUMMARY OF THE INVENTION

The present invention provides a simple and effective process for preparing tocopherol concentrates. The method is characterized by precipitating the free acids in a mixture containing tocopherols and free fatty acids as the alkali metal salts thereof in a specific solvent that cannot, practically, dissolve the alkali metal salts of fatty acids, and recovering the tocopherols from the supernatant by removing the solvent. The specific organic solvents include acetone, ethyl acetate, dimethylformamide, acetonitrile and their mixtures.

BRIEF DESCRIPTION OF THE DRAWINGS

Table 1 The main compositions of the soybean deodorizer sludge and some tocopherol concentrates.

Table 2 The result of gas chromatographic analysis revealed that the tocopherol content with solvent as DMF, acetonitrile or ethyl acetate Table 3 The result of gas chromatographic analysis revealed that the tocopherol content with NaOH

| Peak No. | Tocopherol content (%) | | Peak No. | Phytosterol content (%) | |
|---|---|---|---|---|---|
| 3 | α-tocopherol | 0.45% | 4 | Campesterol | 1.32% |
| 2 | γ-tocopherol | 11.89% | 5 | Stigmasterol | 0.97% |
| 1 | δ-tocopherol | 5.85% | 6 | β-stitosterol | 2.02% |
| | Total | 18.19% | | Total | 4.31% |

Figure 1:
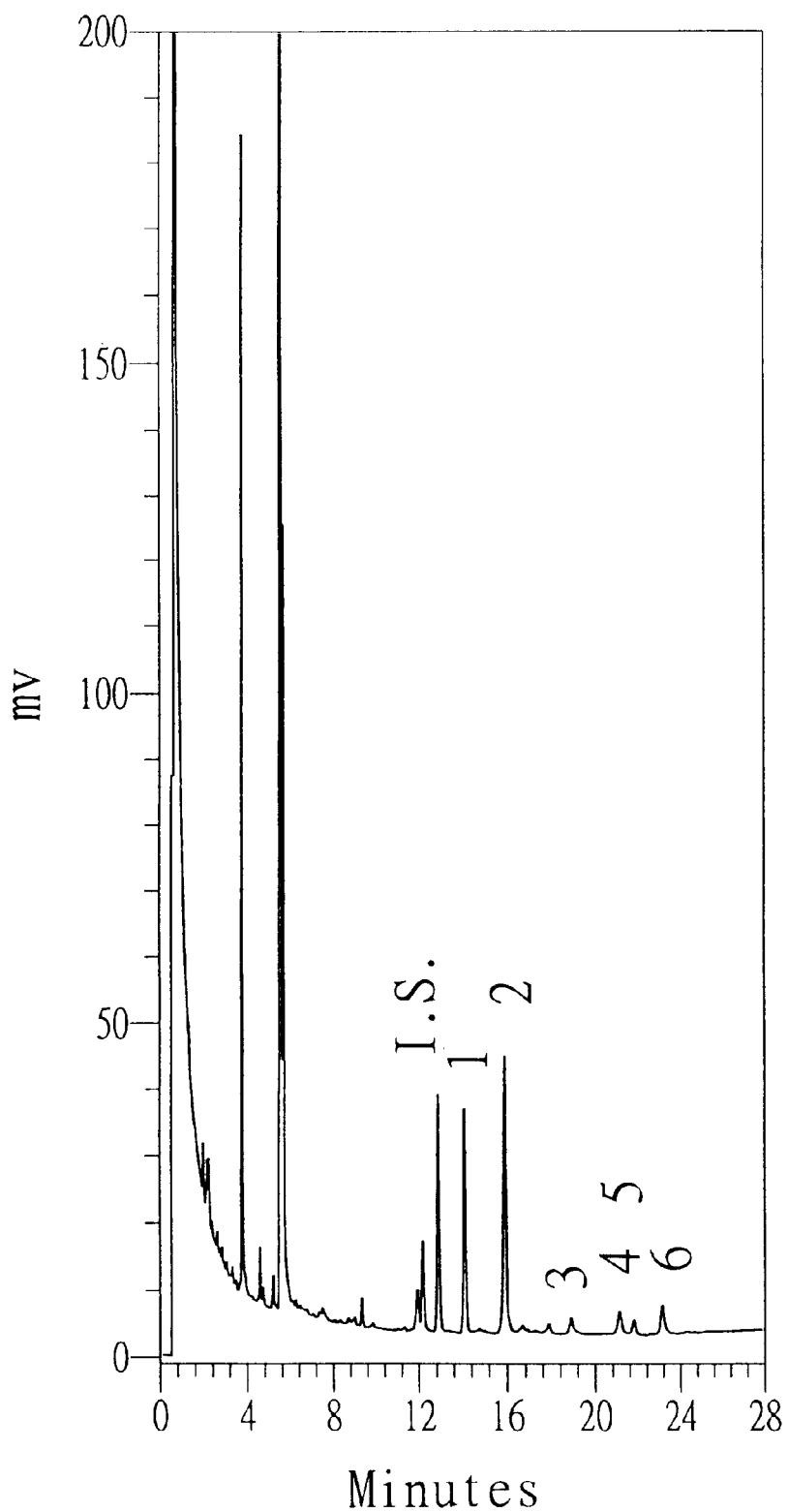
FIG. 1: It illustrates the gas chromatogram of the tocopherols and phytosterols contained in the soybean oil deodorizer sludge.
Figure 2:
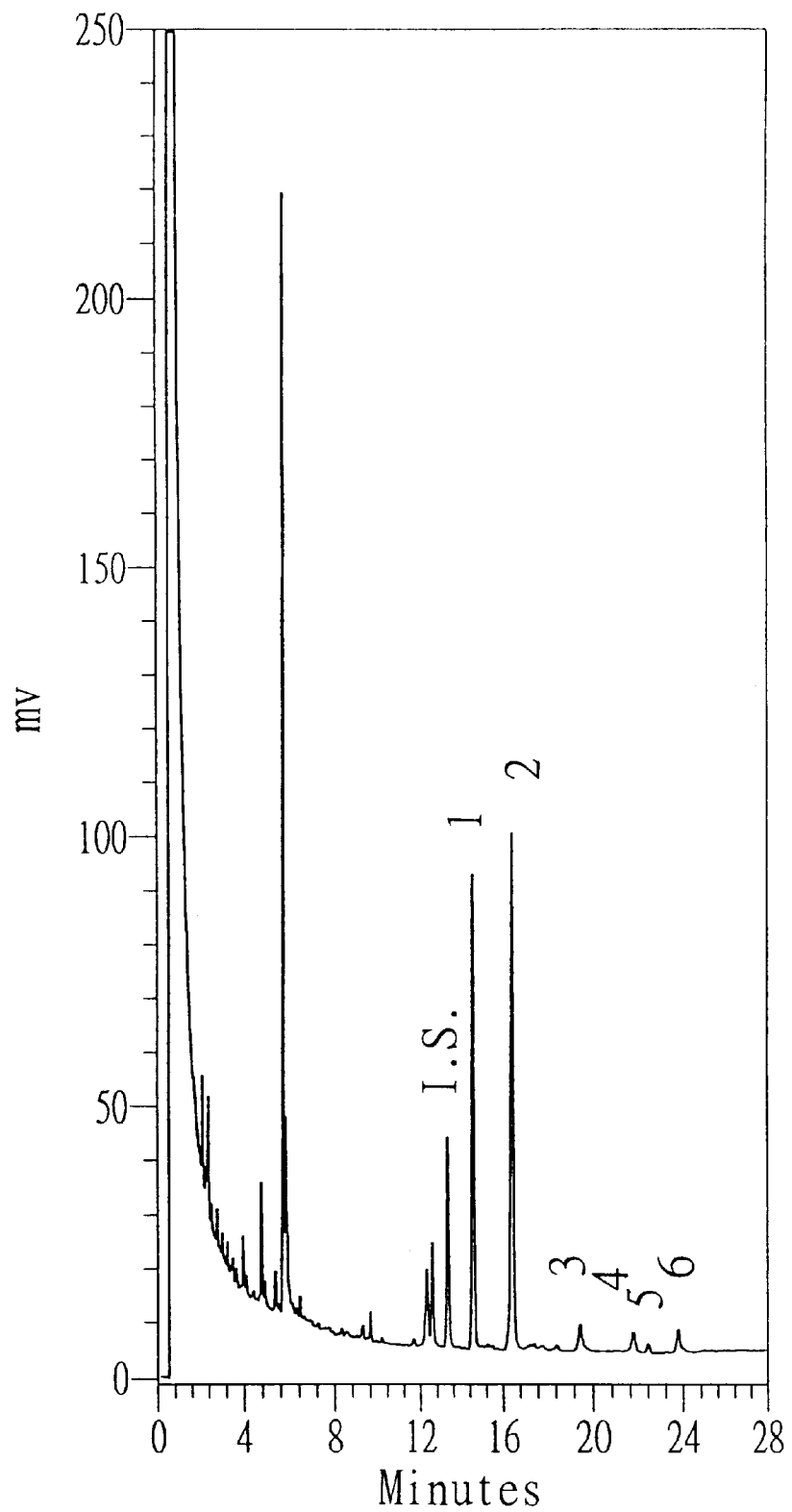

FIG. 2: It illustrates the gas chromatogram of the tocopherols and phytosterols contained in the tocopherol concentrate (Example 1).

| Peak No. | Tocopherol content (%) | | Peak No. | Phytosterol content (%) | |
|---|---|---|---|---|---|
| 3 | α-tocopherol | 1.21% | 4 | Campesterol | 3.67% |
| 2 | γ-tocopherol | 27.38% | 5 | Stigmasterol | 1.75% |
| 1 | δ-tocopherol | 14.47% | 6 | β-stitosterol | 6.34% |
| | Total | 43.06% | | Total | 11.76% |

Figure 3:
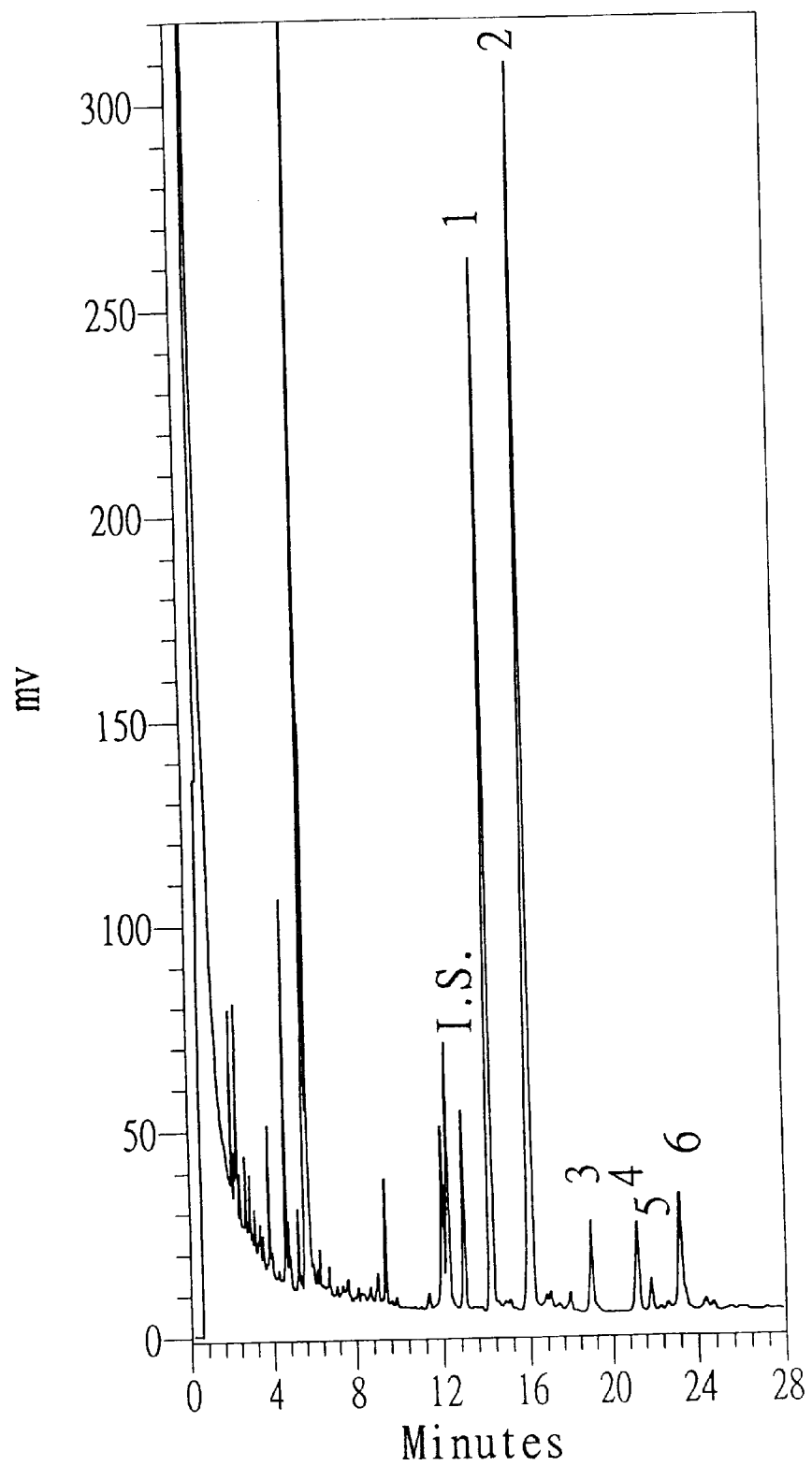

FIG. 3 It illustrates the gas chromatogram of the tocopherols and phytosterols contained in the tocopherol concentrate (Example 5)

| Peak No. | Tocopherol content (%) | | Peak No. | Phytosterol content (%) | |
|---|---|---|---|---|---|
| 3 | α-tocopherol | 2.56% | 4 | Campesterol | 3.78% |
| 2 | γ-tocopherol | 34.74% | 5 | Stigmasterol | 1.98% |
| 1 | δ-tocopherol | 25.88% | 6 | β-stitosterol | 7.62% |
| | Total | 63.18% | | Total | 13.38% |

DETAILED DESCRIPTION OF THE INVENTION

The invention relates to a simple and effective process for preparing tocopherol concentrates from a material containing tocopherols and free fatty acids. The free fatty acids in the mixtures are converted to the alkali metal salts in a specific organic solvent that cannot, practically, dissolve the alkali metal salts of fatty acids. The tocopherols are then recovered from the supernatant by removing the solvent.

The aforesaid mixtures that contain tocopherols and free fatty acids include, for example, vegetable oil deodorizer sludge such as soybean oil deodorizer sludge, palm oil deodorizer sludge, etc. The said specific organic solvent that cannot, practically, dissolve the alkali metal salts of free fatty acids can be, as examples, acetone, ethyl acetate, dimethylformamide, acetonitrile and their mixtures. Among them, acetone and ethyl acetate are preferred, and acetone is especially preferred.

The said alkali metal salts, as examples, can be sodium and potassium salts. Among them, sodium salts are preferred. The alkali used for converting the free fatty acids to their alkali metal salts can be, as examples, sodium hydroxide and potassium hydroxide. Sodium hydroxide is preferred.

The amount of alkali used is about 0.5 to 1.2 equivalents of the free fatty acids in the raw material, and 0.8 to 1.0 equivalents is relatively preferred. When the amount of alkali is too less, the removal of free fatty acids is not satisfactory. On the other hand, when the amount is too much excess, it can not obtain extra efficiency, and will reduce the recovery of tocopherols.

If a considerable fatty acids in the raw material are present in the ester forms, the raw material can be previously subjected to hydrolysis. The hydrolysis can be conducted by chemical hydrolysis such as saponification, alkali-catalytic hydrolysis, etc., or by enzymatic hydrolysis using lipase or esterase.

The solvent volume is about 4 to 10 times of the volume of raw material, and 4 to 6 times is preferred. When the solvent volume is too small, the recovery is low. When the solvent volume is too much, it will be not economic.

The tocopherol concentrates derived from the method of this invention can reach about 32 to 63%. The recoveries of tocopherols are mostly over 80% to 95%. The said tocopherol concentrates can be directly used as the natural antioxidants, nutrients or be used as the raw material for the preparation of further purified tocopherols. In additions, the by-products of alkali metal salts of fatty acids can be directly used for making soap or served as the ingredient of natural detergent for cleaning the foods such as vegetables and fruits. Therefore, the process of this invention can prevent the occurrence of the secondary industrial pollution of by-products. For the aforesaid reasons, this invention is evident of industrial application values.

Quantitative Analysis of Tocopherols and Phytosterols

The quantitative analysis of tocopherols and phytosterols is carried out by the gas chromatography (GC) described as below.

Weigh accurately about 25 mg of the sample or the standard compounds [α-tocopherol (α-toc.), γ-tocopherol (γ-toc.), δ-tocopherol (δ-toc.) campesterol (Camp), stigmasterol (Stig.) and β-sitosterol (β-sito.)] into a small tube with a lid. Add 0.5 mL pyridine, 0.1 mL TFA (trifluoroacetic acid) and 0.5 mL HMDS (hexamethyldisilazane). Let the mixture react at room temperature for 10 minutes. Add 1 mL of internal standard (IS) solution. (0.1 g 5α-cholestane dissolved in 100 mL hexane). Concentrate the reaction mixture by flushing with nitrogen gas to about 0.5 mL and subjected to gas chromatographic analysis.

The analysis conditions are as follows:
Instrument: Variant 3400 GC
Column: DB-1 capillary column (0.53 mm×30 m), splitless
Carrier Gas: H2, 3 mL/min
Detector: FID
Injector temperature: 290° C.
Detector temperature: 320° C.
Column temperature:

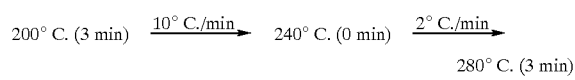

The contents of various tocopherols and phytosterols are determined according to the following equation.

$$X(\%) = \frac{Ax/(RRF)x}{Ais} \times \frac{Wis}{Ws} \times 100\%$$

Wherein,
X: the contents of various tocopherols and phytosterols.
Ax: GC peak areas of various tocopherols and phytosterols.
Ais: GC peak area of the internal standard (IS).
Ws: weight(g) of the sample.
Wis: weight(g) of the internal standard (IS).
(RRF)x: the relative response factor of various tocopherols and phytosterols to the internal standard (IS).

$$(RRF)_x = \frac{A_x/W_x}{A_{IS}/W_{IS}}$$

Wx: weight(g) of various tocopherol standards and phytosterol standards.

EXAMPLES

The present invention is illustrated more in details by referring to the following examples. However, it should be understood that the following examples can not be used to limit the scope of this invention. All modifications, equivalents, and alternatives falling within the spirit of this invention should be included in the claims of this invention.

Example 1

Dissolve 20 g of soybean oil deodorizer sludge (acid value=118; saponification value=147; tocopherol content=18.19%) in 100 mL acetone. Add 1.52 g NaOH (0.9 equivalent of the free fatty acid) dissolved in a little of water while stirring. Thereafter, continue the stirring for 1 hour. Remove the precipitate by centrifugation. Collect the supernatant and remove the solvent to obtain 8.02 g (yield=40.1%) of brown oil. The result of chromatographic analysis is shown in Table 1. The tocopherol content is 43.06% (recovery=94.93%) and the phytosterol content is 11.76%. The saponification value of this product is 82.38, which is corresponding to about 43.36% of free fatty acids.

Example 2

Dissolve 20 g of soybean oil deodorizer sludge (acid value=118; tocopherol content=18.19%) in 100 mL acetone. Add 2.13 g KOH (0.9 equivalent of free fatty acids) dissolved in a little of water while stirring. Thereafter, continue the stirring for 1 hour. Remove the precipitate by centrifugation. Collect the supernatant and remove the solvent to obtain 9.34 g (yield=46.7%) of brown oil. The result of gas chromatographic analysis revealed that the tocopherol content of the product is 32.76% (recovery=84.0%).

Comparison Example 1

Use ethanol to replace the acetone solvent in Example 1. The others are all the same as in Example 1. The result shows that no precipitate occurs.

Comparison Example 2

Use hexane to replace the acetone solvent in Example 1. The others are all the some as in Example 1.

Separate the supernatant and remove the solvent by rotary vacuum distillation. As a result, 12.9 g (yield 63%) of glutinous substance, instead of the liquid tocopherol concentrate, is obtained. No liquid oil of tocopherols can be obtained in this comparison example.

Comparison Example 3

Use methanol to replace the acetone solvent in Example 1. The others are all the same as in Example 1. The result show that no precipitate occurs.

Example 3

Use dimethylformamide (DMF), acetonitrile or ethyl acetate to replace the acetone solvent in Example 1. The others are all the same as in Example 1. The results are as shown in Table 2, indicating that they all can significantly increase the contents of tocopherols.

Example 4

Follow the same steps as in Example 1, but change the amounts of NaOH to 0.8 and 1 equivalent of the free fatty acids, namely 1.35 g and 1.69 g of NaOH, respectively. The results are as shown in Table 3, indicating that they all can significantly increase the contents of tocopherols.

INDUSTRIAL APPLICABILITY

Most of the methods adopted for industrial production of tocopherol concentrates involve the steps of esterification and high-temperature molecular distillation. The steps for such methods are complex and require expensive equipment. Moreover, the high temperature for operating molecular distillation might be a disadvantage to tocopherols. The present invention provides a simple and effective process for preparing tocopherol concentrates which comprises precipitating the free fatty acids in a mixture containing tocopherols and free fatty acids as the alkali metal salts thereof in a specific solvent that cannot, practically, dissolve the alkali metal salts of fatty acids, and recovering the tocopherols from the supernatant by removing the solvent. According to the present invention, the tocopherol concentrates can be easily and economically produced with good recoveries. The tocopherol concentrates derived from the processing method of the present invention can be used directly in food industry, medical field and other industries. It can also be used as the raw materials for producing further highly purified tocopherols. In additions, the alkali metal salts separated as the precipitate can be directly used for the production of soaps or detergents for cleaning the foods such as fruits and vegetables, etc. Therefore, the processing method according to the present invention will cause no secondary industrial pollution.

TABLE 1

The main compositions of the soybean deodorizer sludge and some tocopherol concentrates.

| Composition Sample | Tocopherol (%) | Phytosterol (%) | Fatty acids and their esters (%) |
|---|---|---|---|
| Soybean oil deodorizer sludge | 18.19 | 4.31 | 77.37* |
| Tocopherol concentrate (Example 1) | 43.06 | 11.76 | 43.36* |
| Tocopherol concentrate (Example 5) | 63.08 | 13.38 | 21.87* |

*The contents of fatty acids and their esters are estimated with the suggestion that the saponification value of soybean oil be equal to 190, and the content of free fatty acids and their esters = saponification value of sample/190 × 100%.

The contents of fatty acids and their esters are estimated with the suggestion that the saponification value of soybean oil be equal to 190, and the content of free fatty acids and their esters=saponification value of sample/190×100%.

TABLE 2

| | | Tocopherol | |
|---|---|---|---|
| Solvent | Yield (%) | Content (%) | Recovery (%) |
| DMF | 40.65 | 37.71 | 84.27 |
| Acetonitrile | 15.00 | 35.68 | 29.42 |
| Ethyl Acetate | 50.15 | 35.26 | 97.21 |

TABLE 3

| | Tocopherol | |
|---|---|---|
| Amount of NaOH | Content (%) | Recovery (%) |
| 1.35 g (0.8 equivalent of fatty acids) | 32.58 | 78.79 |
| 1.69 g (1 equivalent of fatty acids) | 38.08 | 82.99 |

What is claimed is:

1. A method for preparing a tocopherol concentrate comprising the steps of: dissolving a mixture containing tocopherols and free fatty acids in a solvent selected from the group consisting of acetone, ethyl acetate, dimethyl formamide, acetonitrile and mixtures thereof; adding alkali metal hydroxides to precipitate the free fatty acids; and recovering the tocopherol concentrate from a supernatant by removing the solvent.

2. The method of claim 1 wherein the mixture containing tocopherols and free fatty acids is vegetable oil deodorizer sludge.

3. The method of claim 2 wherein the vegetable oil deodorizer sludge is soybean oil deodorizer sludge.

4. The method of claim 2 wherein the vegetable oil deodorizer sludge is subjected to water hydrolysis before the dissolving steps.

5. The method of claim 1 wherein the solvent is selected from the group consisting of acetone, ethyl acetate and mixtures thereof.

6. The method of claim 1 wherein the alkali metal hydroxides are selected from the group consisting of sodium hydroxide, potassium hydroxide and mixtures thereof.

7. The method of claim 6 wherein the amount of alkali hydroxides used is equal to between 0.6 and 1.2 times the equivalents of the free fatty acids.

8. The method of claim 6 wherein the amount of alkali metal hydroxides used is equal to between 0.8 and 1.0 times the equivalents of the free fatty acids.

9. The method of claim 1 wherein the amount of the solvent used is equal to between 2 and 10 times the amount of the mixture of tocopherols and free fatty acids, by weight.

10. The method of claim 8 wherein the amount of the solvent used is equal to between 4 and 10 times the amount of the mixture of tocopherols and free fatty acids, by weight.

11. The method of claim 1 wherein the amount of the solvent used is equal to between 4 and 6 times the amount of the mixture of tocopherols and free fatty acids, by weight.

* * * * *